US006395785B1

(12) United States Patent
Södervall et al.

(10) Patent No.: US 6,395,785 B1
(45) Date of Patent: May 28, 2002

(54) E-2-[4-(4-CHLORO-1,2-DIPHENYL-BUT-1-ENYL)PHENOXY]ETHANOL AND PHARMACEUTICAL COMPOSITIONS THEREOF

(75) Inventors: Marja-Liisa Södervall; Arja Kalapudas, both of Oulu; Antti Viitanen, Espoo; Eero Mäntylä, Piispanristi, all of (FI)

(73) Assignee: Orion Corporation, Epoo (FI)

( * ) Notice: Subject to any disclaimer, the term of this patent is extended or adjusted under 35 U.S.C. 154(b) by 0 days.

(21) Appl. No.: 09/601,612
(22) PCT Filed: Feb. 19, 1999
(86) PCT No.: PCT/FI99/00137
 § 371 (c)(1),
 (2), (4) Date: Sep. 7, 2000
(87) PCT Pub. No.: WO99/42427
 PCT Pub. Date: Aug. 26, 1999

(30) Foreign Application Priority Data

Feb. 19, 1998 (GB) ............................................. 9803521

(51) Int. Cl.⁷ ........................ A01N 37/10; C07C 39/205
(52) U.S. Cl. ........................ 514/571; 514/570; 568/641
(58) Field of Search .......................... 568/641; 514/720, 514/721

(56) References Cited

U.S. PATENT DOCUMENTS

| 4,996,225 A | 2/1991 | Toivola et al. ............... 514/428 |
| 5,750,576 A | 5/1998 | DeGregorio et al. ......... 514/720 |

FOREIGN PATENT DOCUMENTS

| WO | WO 96/07402 | 3/1996 | ......... A61K/31/075 |
| WO | WO 97/32574 | 9/1997 | ......... A61K/31/085 |

OTHER PUBLICATIONS

Koedijk et al., Comparative Affinity . . . Site, Biochem. Pharmacol., vol. 43, No. 12, pp. 2511–2518, 1992.*

* cited by examiner

*Primary Examiner*—Rosalynd Keys
(74) *Attorney, Agent, or Firm*—Burns, Doane, Swecker & Mathis, L.L.P.

(57) ABSTRACT

The present invention relates to E-2-[4-(chloro-1,2-diphenyl-butleny1)phenoxy]ethanol which is useful in lowering serum cholesterol and to pharmaceutical compositions thereof. The invention also describes methods of lowering serum cholesterol and methods for the prevention of or the treatment of atherosclerosis.

5 Claims, No Drawings

E-2-[4-(4-CHLORO-1,2-DIPHENYL-BUT-1-ENYL)PHENOXY]ETHANOL AND PHARMACEUTICAL COMPOSITIONS THEREOF

This application is a 371 of PCT/F199/00137, filed Feb. 19, 1999.

The present invention relates to E-2-[4-(4-chloro-1,2-diphenyl-but-1-enyl)phenoxy]ethanol (I) having serum cholesterol lowering properties and to pharmaceutical compositions thereof. Compound (I) is useful in reducing serum cholesterol levels and in the treatment of atherosclerosis. It is also potentially useful in the hormone replacement therapy (HRT).

It has been demonstrated that elevated levels of serum cholesterol associated with low density lipoproteins (LDL) are a major contributing factor in the development and progression of atherosclerosis. Therefore it is desirable to provide a method for reducing serum cholesterol levels in patients with hypercholesterolemia or at risk of developing hypercholesterolemia.

International patent application WO97/32574 describes the use of Z-2-[4-(4-chloro-1,2-diphenyl-but-1-enyl)phenoxy]ethanol for lowering serum cholesterol. The compound has no significant estrogenic side effects in uterine tissue but is able to block the adverse effects of estrogen on uterus. Therefore this compound is especially useful in lowering serum cholesterol. The corresponding E-isomer is not described in this patent application.

Z-2-[4-(4-chloro-1,2-diphenyl-but-1-enyl)phenoxy]ethanol is a metabolite of known antiestrogen drug toremifene. Toremifene (Z-4-chloro-1,2-diphenyl-1-[4-[2-(N,N-dimethylamino)ethoxy]-phenyl]-1-butene) is currently used clinically for the treatment of estrogen receptor positive breast cancer.

Now it has been found that E-2-[4-(4-chloro-1,2-diphenyl-but-1-enyl)phenoxy]ethanol (I) is significantly more potent in lowering serum total cholesterol but approximately equal in uterine effects when compared to the corresponding Z-isomer. This was unexpected since the E-isomer of toremifene is purely estrogenic in uterine tissue. Furthermore, it has been found that the E-isomer of the invention is able to inhibit cholesterol biosynthesis directly whereas the corresponding Z-isomer has not such effect.

Thus, E-2-[4-(4-chloro-1,2-diphenyl-but-1-enyl)phenoxy]ethanol (I) is especially useful in lowering serum cholesterol and in the prevention or treatment of atherosclerosis. Compound (I) is also potentially useful in the hormone replacement therapy (HRT).

Accordingly, the invention provides a novel compound useful in lowering serum cholesterol levels said compound being E-2-[4-(4-chloro-1,2-diphenyl-but-1-enyl)phenoxy]ethanol and having the structure (I)

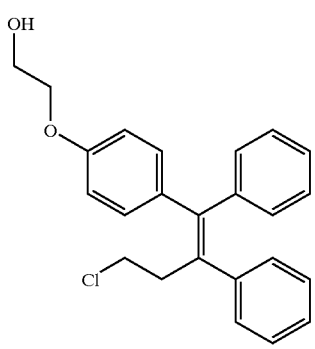

(I)

or a pharmaceutically acceptable ester thereof.

Pharmaceutically acceptable esters include esters made with aliphatic carboxylic acids, preferably $C_{1-6}$ acids, e.g. acetic acid, and made with aroma-tic carboxylic acids, e.g. $C_{7-12}$ acids such as benzoic acid. The aliphatic and aromatic acids may optionally be substituted by e.g. one or more $C_{1-4}$ alkyl.

The invention also provides a pharmaceutical composition comprising E-2-[4-(4-chloro1,2-diphenyl-but-1-enyl)phenoxy]ethanol or a pharmaceutically acceptable ester thereof as an active ingredient together with a pharmaceutically acceptable carrier.

The invention also provides a method of lowering serum cholesterol levels which method comprises administering to a patient in need of such treatment an effective amount of E-2-[4-(4-chloro-1,2-diphenyl-but-1-enyl)phenoxy]ethanol or a pharmaceutically acceptable ester thereof.

The invention also provides a method for the prevention or treatment of atherosclerosis which method comprises administering to a patient in need of such treatment an effective amount of E-2-[4-(4-chloro-1,2-diphenyl-but-1-enyl)phenoxylethanol or a pharmaceutically acceptable ester thereof.

The invention also provides a method of hormone replacement therapy (HRT) which method comprises administering to a patient in need of such therapy an effective amount of E-2-[4-(4-chloro-1,2-diphenyl-but-1-enyl)phenoxylethanol or a pharmaceutically acceptable ester thereof.

The compound of the invention may be administered in a variety of ways including orally, parenterally or transdermally using conventional forms of preparations, such as capsules, tablets, granules, powders, suppositories, injections, patches, suspensions and syrups. The term "effective amount" means an amount of compound of the invention which is capable of lowering serum total cholesterol levels or capable of blocking the adverse effects of estrogen particularly on uterus or inhibiting menopausal symptoms. The compound of the invention may be administered according to the method of the invention monthly, weekly or daily or several times a day depending upon the patient's needs. A typical daily oral dosage is within the range of from about 0.5 mg to about 1000 mg, preferably from about 10 mg to about 800 mg, of the active compound. However, the dosage may be properly varied depending on the age, body weight and conditions of the patient as well as on the administration method. The compound of the invention may be administered alone or together with other active compounds.

The compositions according to the invention can be prepared by the methods commonly employed in the art. In addition to the active compound the compositions may contain pharmaceutically acceptable additives commonly used in the art, such as carriers, binders, excipients, lubricants, suspending agents and diluents. The amount of the active compound in the compositions of the invention is sufficient to produce the desired therapeutic effect, for example about 0.5 to 1000 mg, preferably about 10 mg to 800 mg, in unit dosage for both oral and parenteral administration.

The following examples illustrate the synthesis of the compound of the invention.

EXAMPLES

Example 1.

Preparation of E-2-[4-(4chloro-1,2-diphenyl-but-1 enyl)phenoxy]ethanol a) E-4-[4-(2-benzyloxyethoxy)phenyl]-3,4-diphenyl-but-3-en-1-ol The alkylation of the starting phenol with benzyl-(2-bromoethyl)ether was carried out as described in Example 1 of the International Patent Application WO 96/07402 with the exception that now the starting compound was the other geometric isomer, E-4-(4-hydroxy-1,2-diphenyl-but-1-enyl)-phenol which was prepared by the method described in U.S. Pat. No. 4,996,225. The product was extracted to toluene. The toluene phases were combined, washed with water, dried and evaporated to dryness. The residue was recrystallized from a minor quantity of toluene and the precipitated product was used in the next step without further purification.

$^1$H NMR (300 MHz, CDCl$_3$): 2.8 (2H, t, CH$_2$—C=), 3.6 (2H, dt, CH$_2$OH), 3.8 (2H, t, CH$_2$OBn), 4.2 (2H, t, CH$_2$OPh), 4.6 (2H, s, OCH$_2$Ph), 6.8–7.4 (19H, m).

b) E-1-[4-(2-benzyloxyethoxy)phenyl]-4-chloro-1,2-diphenyl-but-1-ene

The halogenation of E-4-[4-(2-benzyloxyethoxy)phenyl]-3,4-diphenyl-but-3-en-1-ol was carried out as described in Example 2 of the International Patent Application WO 96/07402 but using E-4-[4-(2-benzyloxyethoxy)-phenyl]-3,4-diphenyl-but-3-en-1-ol as the starting compound.

$^1$H NMR (300 MHz, CDCl$_3$): 3.0 (2H, t), 3.4 (2H, t), 3.8 (2H, t), 4.2 (2H, t), 4.6 (2H, s), 6.9–7.4 (19H, m).

c) E-2-[4-(4-chloro-1,2-diphenyl-but-1-enyl)phenoxy]ethanol 6.9 g of E-1-[4-(2-benzyloxyethoxy)phenyl]-4-chloro-1,2-diphenyl-but-1-ene was dissolved in the mixture of ethyl acetate (60 ml) and ethanol (60 ml). Palladium on carbon (5%, 0.7 g) was added and the solution was stirred vigorously under a hydrogen atmosphere at room temperature until there was not any starting compound left (thin layer chromatography). Palladium on carbon was filtered off through siliceous earth and the filtrate was evaporated to dryness. The residue was crystallized several times from the mixture of ethanol and water.

$^1$H NMR (300 MHz, CDCl$_3$): 3.0 (2H, t), 3.4 (2H, t), 4.0 (2H, m), 4.1 (2H, t), 6.8–7.3 (14H, m).

MS-spectrum (+EI, 70 eV, direct inlet): 378 (100%), 342 (8%), 329 (43%), 285 (23%), 284 (28%), 207 (32%), 191 (30%).

EXPERIMENTS

Methods

The estrogenic/antiestrogenic activity of the study drug was tested by measuring the effect on the uterine weight in immature (18 days old) female Sprague-Dawley rats. The compound was given p.o. in a PEG-solution for 3 days (n=5/group). At the same time the ability of the study drug to inhibit estrogen-induced increase in uterine weight was studied in rats given estradiol 50 µg/kg s.c. Comparison was made with the corresponding Z-isomer.

The effects on cholesterol biosynthesis was studied in vitro in Hep G2 cell cultures using $^{14}$C-acetate as cholesterol precursor. The test compound was added into the culture medium at concentrations from 0.01 to 10 micromolar. After 2 hours the culture was stopped and the newly synthesized cholesterol was quantitated by thin-layer chromatography. Comparison was made with the Z-isomer.

The effects on uterine weight and on serum cholesterol levels were studied in intact and ovarectomized adult female Sprague-Dawley rats. In the intact rats the study drug was given p.o. at a daily dose of 3.17 mg/kg for two weeks and comparison was made with the equimolar doses of the Z-isomer, toremifene Eisomer, raloxifene or estradiol. In the ovarectomy study the study drug was given p.o. at a daily dose of 0.1, 1 or 10 mg/kg for 4 weeks and comparison was made with the corresponding Z-isomer and estradiol (100 µg/kg). The serum cholesterol content was determined by an enzymatic method. In the ovarectomy study the serum cholesterol and cholesterol precursor molecule content was determined by gas-liquid chromatography.

Results

In the immature rat uterine weight test the E-isomer of the invention showed approximately equal estrogenic and anti-estrogenic effect when compared to the corresponding Z-isomer. The results are shown in Table 1 wherein 1271b (E) means the E-isomer of the invention, 1271a (Z) means the corresponding Z-isomer and E2 means estradiol.

TABLE 1

| Drug dose | Average uterine weight (weight after mere E2-treatment was taken as 1.00) | | | |
|---|---|---|---|---|
| (mg/kg) | 1271a (Z) | 1271a (Z) + E2 | 1271b (E) | 1271b (E) + E2 |
| 0 | 0.25 | 1.00 | 0.33 | 1.00 |
| 0.1 | 0.27 | 1.18 | 0.37 | 0.81 |
| 0.5 | 0.43 | 1.11 | 0.45 | 0.82 |
| 1 | 0.53 | 0.91 | 0.44 | 0.57 |
| 10 | 0.75 | 0.91 | 0.75 | 0.83 |

In the in vitro cell culture system used the E-isomer of the invention inhibited slightly cholesterol biosynthesis but the Z-isomer had an opposite effect as shown in Table 2.

TABLE 2

| Drug concentration | Cholesterol biosynthesis level (% of control) | |
|---|---|---|
| (µM) | 1271a (Z) | 1271b (E) |
| 0.01 | 143 | 89 |
| 0.1 | 127 | 90 |
| 1 | 129 | 89 |
| 10 | 132 | 84 |

In adult female rats 1271b (E), 1271a (Z) and raloxifene decreased relative uterine weight at about the same extent. Instead, estradiol and toremifene E-isomer increased the weight. Of the drugs 1271b (E), toremifene E-isomer, raloxifene and estradiol decreased serum cholesterol level with an approximately equal efficacy (by 50–60%). The 1271a (Z) molecule was less effective. The results are shown in Table 3.

TABLE 3

| | Relative uterine weight and serum cholesterol content (control level has been taken as 1.00; mean ± SD, n = 3) | |
|---|---|---|
| Drug molecule | Uterus | Cholesterol |
| 1271b (E) | 0.85 ± 0.07 | 0.43 ± 0.05 |
| 1271a (Z) | 0.75 ± 0.06 | 0.65 ± 0.10 |
| Toremifene (E) | 1.09 ± 0.10 | 0.40 ± 0.18 |
| Raloxifene | 0.77 ± 0.21 | 0.48 ± 0.09 |
| Estradiol | 1.29 ± 0.06 | 0.48 ± 0.09 |

In the ovarectomy study 1271b (E) increased slightly (1.5-fold) the relative uterus weight, not more than the corresponding Z-isomer. Estradiol increased the weight 3.3-fold. The 1271b (E) decreased serum cholesterol level very efficiently (by up to 77%), 1271a (Z) was clearly less effective (decrease was up to 34%). The results are shown in Table 4.

TABLE 4

| Drug dose (mg/kg) | Relative uterine weight and serum cholesterol content (control level has been taken as 1.00) | | | |
|---|---|---|---|---|
| | 1271b (E) Uterus | Cholesterol | 1271a (Z) Uterus | Cholesterol |
| 0.1 | 1.54 | 0.92 | 1.22 | — |
| 0.5 | — | — | — | 0.90 |
| 1 | 1.50 | 0.62 | 1.78 | 0.96 |
| 5 | — | — | — | 0.89 |
| 10 | 1.53 | 0.23 | 2.04 | 0.66 |

Further, in the ovarectomy study it was noticed that 1271b (E) but not 1271a (Z) increased slightly serum cholesterol precursor molecule level suggesting a direct cholesterol biosynthesis inhibition by 1271b (E).

Discussion

The above data indicate that both 1271a (Z) and 1271b (E) are equivalent in antiestrogenicity in rat uterus. This differs from toremifene as toremifene's E-isomer is clearly estrogenic in rat uterus and the Z-isomer is antiestrogenic. 1271b (E) is more efficient as a hypolipidemic agent than the corresponding Z-isomer. This is at least partly explained by the ability of 1271b (E) to inhibit cholesterol biosynthesis directly. In summary, the test compound 1271b (E) is an antiestrogenic drug that has also beneficial and potent hypolipidemic properties.

What is claimed is:

1. E-2-[4-(4-chloro-1,2-diphenyl-but-1-enyl)phenoxy]ethanol or a pharmaceutically acceptable ester thereof.

2. A pharmaceutical composition which comprises E-2-[4-(4-chloro-1,2-diphenyl-but-1-enyl)phenoxy]ethanol or a pharmaceutically acceptable ester thereof as an active ingredient together with a pharmaceutically acceptable carrier.

3. A method of lowering serum cholesterol levels which method comprises administering to a patient in need of such treatment an effective amount of E-2-[4-(4-chloro-1,2-diphenyl-but-1-enyl)phenoxy]ethanol or a pharmaceutically acceptable ester thereof.

4. A method for the prevention or treatment of atherosclerosis which method comprises administering to a patient in need of such treatment an effective amount of E-2-[4-(4-chloro-1,2-diphenyl-but-1-enyl)phenoxy]-ethanol or a pharmaceutically acceptable ester thereof.

5. A method of hormone replacement therapy (HRT) which method comprises administering to a patient in need of such therapy an effective amount of E-2-[4-(4-chloro-1,2-diphenyl-but-1-enyl)phenoxy]ethanol or a pharmaceutically acceptable ester thereof.

* * * * *